United States Patent [19]
Krespi

[11] Patent Number: 5,460,626
[45] Date of Patent: Oct. 24, 1995

[54] TONGUE BLADE EVACUATION SYSTEM

[75] Inventor: Yosef P. Krespi, New York, N.Y.

[73] Assignee: Laser Industries, Ltd., Tel-Aviv, Israel

[21] Appl. No.: 223,986

[22] Filed: Apr. 6, 1994

[51] Int. Cl.[6] ................................................ A61B 1/26
[52] U.S. Cl. ............................ 606/1; 604/35; 600/241
[58] Field of Search .................................. 606/1; 604/35; 128/10, 11, 15, 16

[56] References Cited

U.S. PATENT DOCUMENTS

| | | | |
|---|---|---|---|
| 3,626,471 | 12/1971 | Florin | 128/16 X |
| 3,768,477 | 10/1973 | Anders et al. | 128/15 X |
| 4,148,308 | 4/1979 | Sayer | 128/15 |
| 4,947,896 | 8/1990 | Bartlett | 128/11 |
| 5,167,622 | 12/1992 | Muto | 604/35 |
| 5,287,848 | 2/1994 | Cubb et al. | 128/11 |

Primary Examiner—Peter A. Aschenbrenner
Attorney, Agent, or Firm—Cobrin Gittes & Samuel

[57] ABSTRACT

An apparatus for and a method of removing smoke and vaporized tissue from a patient's mouth and controlling a patient's tongue through use of a hollow tongue blade coupled to a pneumatic evacuation device which can be used in conjunction with a pharyngeal handpiece during laser applications.

4 Claims, 1 Drawing Sheet

TONGUE BLADE EVACUATION SYSTEM

FIELD OF THE INVENTION

This invention relates generally to the field of surgical instrumentation and more particularly, to a tongue blade device for evacuating vaporized tissue from a patient's mouth during oral laser surgery.

BACKGROUND OF THE INVENTION

Surgical lasers, particularly $CO_2$ lasers are presently used for cutting or ablating tissues in various confined body cavities. One recently developed application of lasers is in the treatment of snoring. A common cause of snoring is a long uvula (the small, conical, fleshy mass of tissue suspended from the center of the soft palate above the back of the tongue) and redundant soft pallet that vibrates during respiration. Occasionally, snoring is accompanied by an enlargement of the tonsils. In the surgical treatment of snoring, the surgeon performs a vertical resection of the soft palate on both sides of the uvula, sparing the uvula itself, with further ablation with the laser of the lateral and inferior sides of the uvula to create a "new uvula" that is higher and smaller (uvulopalatoplasty). Surgical lasers are also used for reshaping or removing the tonsils (tonsillectomy), and for removing or reshaping posterior parts of the tongue (glossectomy).

During such applications of surgical lasers it is desirable and necessary that the work area be maintained as free from smoke and vaporized tissue as possible. It is also necessary that the patient's tongue be kept away from working area. These requirements are necessary to provide a clear view of the working area for the surgeon, and to prevent contamination of the lens included in such apparatus that is used for focussing or defocussing the laser beam on the working area.

While a pharyngeal handpiece typical of the prior art, removes some of the smoke and vaporized tissue during laser applications, it does not remove it rapidly enough to keep the area fully visible for the doctor or to prevent contamination of the lens. Additionally, while a prior art tongue depressor prevents the patient's tongue from interfering with the operation, it occupies one of the surgeon's hands while accomplishing very little. Further, while the foregoing problems are particularly troublesome with respect to the above described applications for surgical lasers, they are also present to some degree in many other applications of surgical lasers.

It is accordingly an object of the present invention to provide a tongue blade evacuation device for eliminating or reducing the foregoing problems during surgical laser applications.

It is another object of the invention to provide a more efficient system for controlling a patient's tongue and for removing smoke and vaporized tissue from a patient's mouth during laser surgery.

It is another object of the invention to provide a device to be used in conjunction with a pharyngeal handpiece to increase the rate of smoke and vaporized tissue evacuation from a patient's mouth during laser surgery.

It is still another object of the invention to provide a method of controlling a patient's tongue and evacuating smoke and vaporized tissue from a patient's mouth during laser surgery.

SUMMARY OF THE INVENTION

The foregoing objects are attained by the invention, which provides an apparatus for and a method of removing smoke and vaporized tissue from a patient's mouth and controlling a patient's tongue through use of a hollow tongue blade coupled to a pneumatic evacuation device which can be used in conjunction with a pharyngeal handpiece during laser applications. The invention includes a hollow tongue blade coupled in pneumatic communication with a hollow handle that is coupled in pneumatic communication with a hollow y-connector, wherein the hollow y-connector is connectable to a pharyngeal handpiece and to a pneumatic evacuation device. The hollow tongue blade has at least one port for receiving smoke or vaporized tissue.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and accompanying drawings, in which.

DETAILED DESCRIPTION OF THE INVENTION

Figure 1:
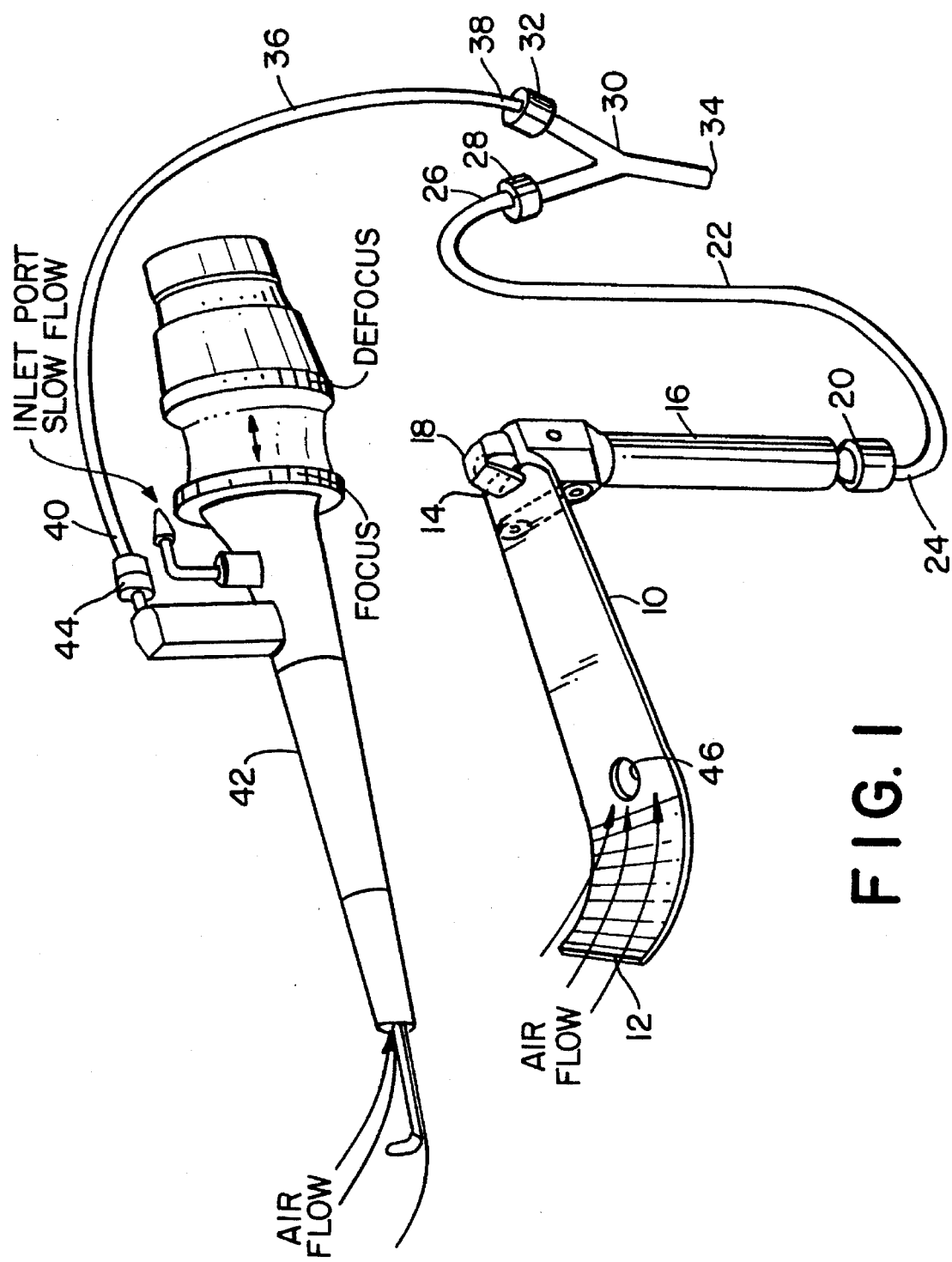
FIG. 1 is a three-dimensional view depicting a tongue blade evacuation system in accordance with the invention; showing details of the hollow tongue blade coupled to a hollow handle which is connected through a flexible conduit to an input port of a hollow y-connector and a pharyngeal handpiece connected through a flexible conduit to a second input port of the hollow y-connector.

FIG. 1 is an illustration of an embodiment of the invention including a hollow tongue blade 10 having a distal end 12 for inserting into a patient's mouth during a laser application and a proximal end 14 coupled in pneumatic communication with a hollow handle 16 at handle input 18; the hollow handle 16 further having a handle output 20 coupled in pneumatic communication with a first flexible conduit 22 at a first conduit input 24; the first flexible conduit 22 further having a first conduit output 26 coupled in pneumatic communication with a hollow y-connector 30 at a first y-input 28; the hollow y-connector 30 further having a second y-input 32 and y-output 34. In the embodiment illustrated, the second y-input 32 is coupled in pneumatic communication with a second flexible conduit 36 at a second conduit output 38, the second flexible conduit 36 further having a second conduit input 40 coupled in pneumatic communication with a pharyngeal handpiece 42 at pharyngeal handpiece exhaust port 44. Further, in the embodiment illustrated in FIG. 1, the hollow tongue blade 10 has a receiving port 46 located proximal to the proximal end 12 for removing smoke, vaporized tissue and other debris from a patient's mouth during use. While in the illustrated embodiment only one receiving port 46 is shown it is possible to have a number of different receiving ports.

When in use, tongue control and smoke and vaporized tissue removal is effectuated by attaching y-output 34 to a pneumatic device typical of the art which causes a suction effect from the hollow tongue blade 10 and from the pharyngeal handpiece 42. The pharyngeal handpiece 42 is connected to a laser (typically a $CO_2$ laser) via laser port 50 for performing the laser application.

While the laser application is taking place, the pharyngeal handpiece 42, which is held in one of the doctor's hands, is held in the patient's mouth directing the laser and removing smoke and vaporized tissue. The hollow tongue blade 10, which the doctor holds in his/her other hand at hollow handle 16, is in the patient's mouth controlling the patient's tongue thus preventing it from obstructing the application and removing smoke and vaporized tissue at the same time. The hollow tongue blade 10 evacuates the smoke and vaporized tissue caused by the laser by sucking it through the receiving port 46, through the hollow handle 16, through the first flexible conduit 22, through the hollow y-connector 30 and out through the pneumatic device.

It will thus be seen that the invention efficiently attains the objects set forth above, among those made apparent from the preceding description. In particular, the invention provides a tongue blade evacuation device for controlling a patient's tongue and removing smoke and vaporized tissue from a patient's mouth during laser applications. Those skilled in the art will appreciate that the configuration depicted in FIG. 1 removes smoke and vaporized tissue efficiently and effectively.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A tongue blade evacuation system for laser applications which is connectable to a laser source, and which is connectable to a pneumatic evacuation device, said system comprising:

a hollow tongue blade including a receiving port, wherein the receiving port pneumatically communicates into said hollow tongue blade, a distal end portion, and a proximal end portion, wherein said receiving port is located proximal said distal end portion on a top portion of said hollow tongue blade;

a hollow handle coupled to said hollow tongue blade, wherein said proximal end portion of said hollow tongue blade is in pneumatic communication with said hollow handle;

a first flexible conduit coupled to said hollow handle, said first flexible conduit being in pneumatic communication with said hollow handle;

a hollow y-connector comprising a first y-input, a second y-input and a y-output, said hollow y-connector being coupled to said first flexible conduit, said first y-input being in pneumatic communication with said first flexible conduit and said y-output being connectable to a pneumatic evacuation device;

a second flexible conduit coupled to said y-connector, said second flexible conduit being in pneumatic communication with said second y-output; and, a handpiece for directing laser radiation into a patient's mouth and removing smoke and vaporized tissue therefrom, said handpiece having a laser port for connecting said handpiece to a laser source, having a lens within said handpiece for selectively focussing and defocussing radiation from said laser source and having an exhaust port, said handpiece being coupled to said second flexible conduit such that said exhaust port is in pneumatic communication with said second flexible conduit.

2. A tongue blade evacuation system for laser applications which is connectable to a laser source, and which is connectable to a pneumatic evacuation device, said system comprising:

a hollow tongue blade having a receiving port, wherein the receiving port pneumatically communicates into said hollow tongue blade;

a hollow handle coupled to said hollow tongue blade such that said hollow handle is in pneumatic communication with said hollow tongue blade;

a hollow y-connector comprising a first y-input, a second y-input and a y-output, said hollow y-connector being coupled to said hollow handle, said first y-input being in pneumatic communication with said first flexible conduit and said y-output being connectable to a pneumatic evacuation device;

a handpiece for directing laser radiation into a patient's mouth and removing smoke and vaporized tissue therefrom, said handpiece having a laser port for connecting said handpiece to a laser source, having a lens within said handpiece for selectively focussing and defocussing radiation from said laser source and having an exhaust port, said handpiece being coupled to said second y-input such that said exhaust port is in pneumatic communication with said second y-input.

3. A method of controlling a patient's tongue and removing smoke and vaporized tissue from a patient's mouth during laser applications comprising the following steps:

coupling a y-output of a hollow y-connector with a pneumatic evacuation device;

coupling a first y-input of said hollow y-connector with a hollow tongue blade, wherein said hollow tongue blade has a receiving port for receiving smoke or vaporized tissue;

coupling a second y-input of said hollow y-connector with a pharyngeal handpiece;

coupling said pharyngeal handpiece with a laser, activating the pneumatic evacuation device so that air is being extracted from the tongue blade and the pharyngeal handpiece;

placing both the hollow tongue blade and the pharyngeal handpiece into the patient's mouth.

4. A method of controlling a patient's tongue and removing smoke and vaporized tissue from a patient's mouth during laser applications according to claim 3 wherein said hollow tongue blade is coupled with said first y-input by attaching a first input of a first conduit to a hollow handle at a handle output and attaching a first output of said first flexible conduit to said first y-input; and, said pharyngeal handpiece is coupled with said second y-input by attaching a second input of a second conduit to said pharyngeal handpiece at a pharyngeal handpiece exhaust port and attaching a second output of said second flexible conduit to said second y-input.

* * * * *